United States Patent
Akahoshi

(10) Patent No.: US 9,668,920 B2
(45) Date of Patent: Jun. 6, 2017

(54) APPARATUS AND METHOD FOR CORNEAL MARKING

(75) Inventor: Takayuki Akahoshi, Tokyo (JP)

(73) Assignee: Art, Limited (KY)

( * ) Notice: Subject to any disclaimer, the term of this patent is extended or adjusted under 35 U.S.C. 154(b) by 1748 days.

(21) Appl. No.: 12/581,665

(22) Filed: Oct. 19, 2009

(65) Prior Publication Data

US 2014/0330297 A1    Nov. 6, 2014

(51) Int. Cl.
*A61F 9/013* (2006.01)

(52) U.S. Cl.
CPC .................. *A61F 9/0136* (2013.01)

(58) Field of Classification Search
CPC ............ A61F 9/007; A61F 2009/00872; A61F 9/0136
See application file for complete search history.

(56) References Cited

U.S. PATENT DOCUMENTS 5,674,233 A * 10/1997 Dybbs ................... A61F 9/0133
                                                               128/898
5,752,967 A *  5/1998 Kritzinger ........... A61F 9/00802
                                                               606/160

* cited by examiner

*Primary Examiner* — Katherine M Shi
*Assistant Examiner* — Michael Mendoza
(74) *Attorney, Agent, or Firm* — Wood, Phillips, Katz, Clark & Mortimer

(57) ABSTRACT

A corneal marking system and methods for its use, has a first tilt-detecting device attached to a corneal marker, adapted to produce a signal when the corneal marker is in a horizontal position. In another version, the first tilt-detecting device is adapted to produce a signal when the corneal marker is in tilted to a pre-selected value and a second tilt-detecting device is attached to the patient's head to measure the tilt of the head and is adapted to produce a signal when the head is tilted to match the pre-selected value of the first tilt-detecting device. In a third version, the first and second tilt detectors send signals to a signal detector which emits a signal when the first and second tilt detectors indicate substantially the same amount of tilt. In each case, the cornea is marked when the appropriate signal is emitted.

13 Claims, 4 Drawing Sheets

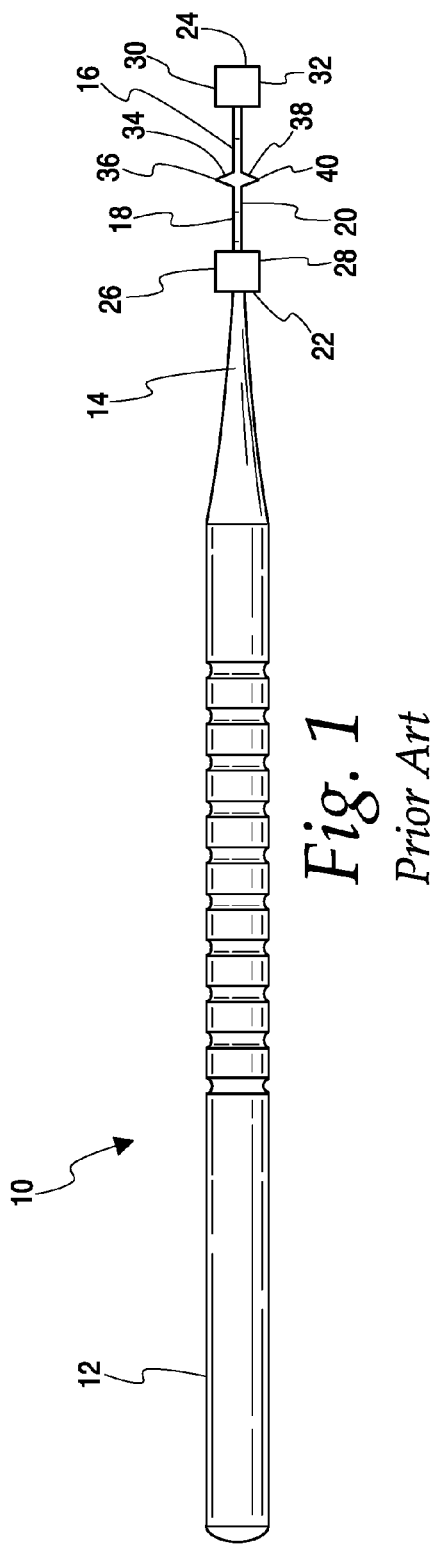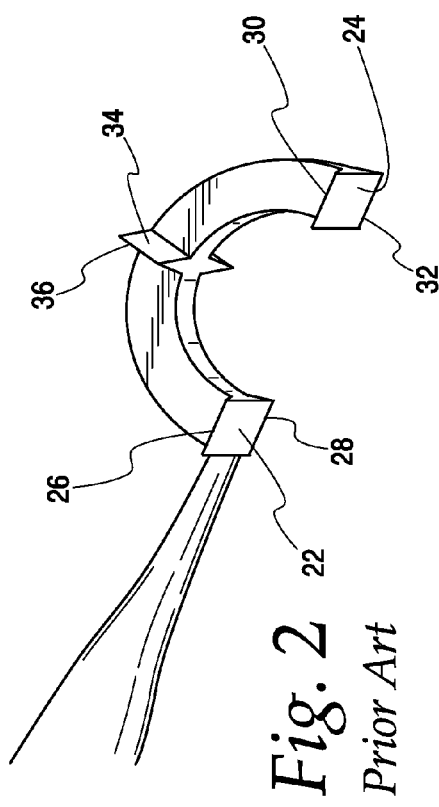

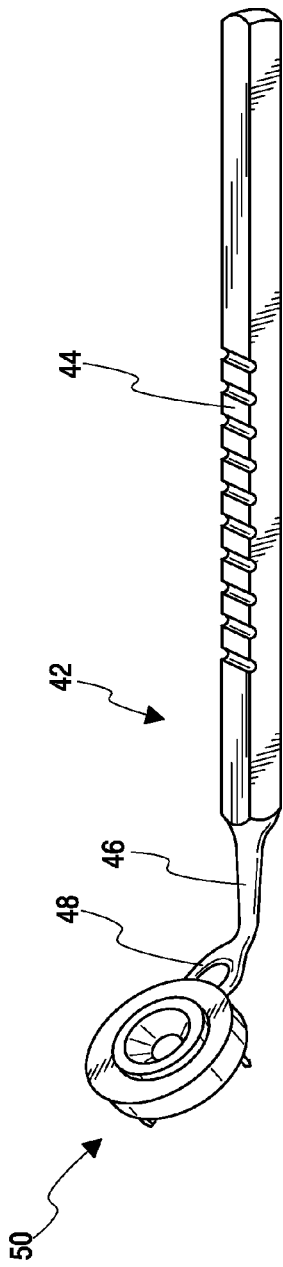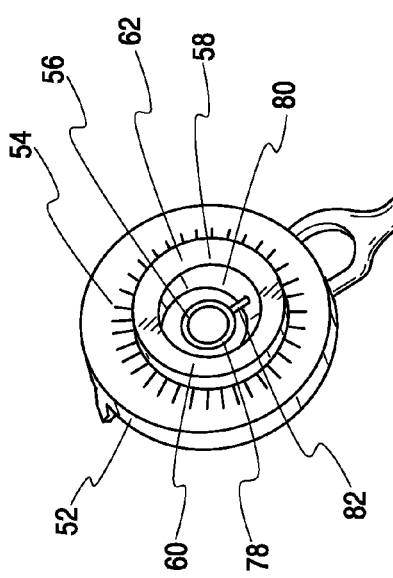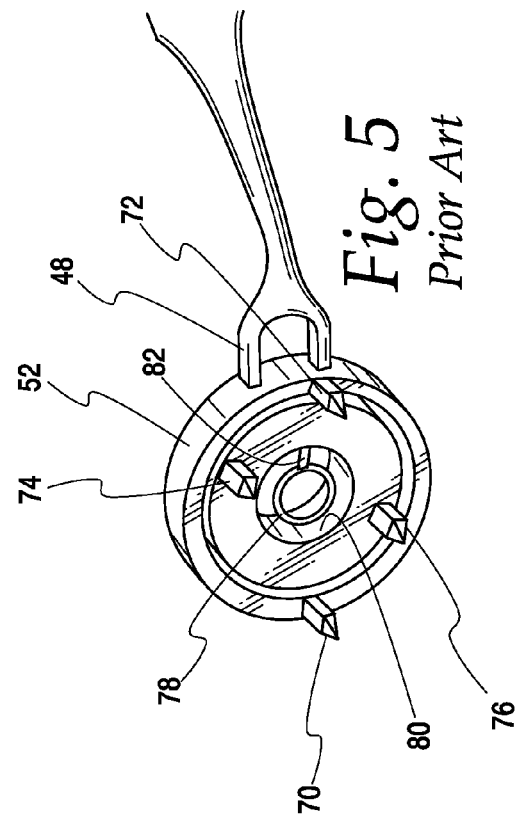

APPARATUS AND METHOD FOR CORNEAL MARKING

BACKGROUND OF THE INVENTION

The present invention relates generally to instruments used in ophthalmic surgery and, more particularly, to instruments used to mark the cornea prior to the implantation and alignment of an intraocular lens (IOL).

Replacement of a cataract with an artificial IOL is now a well-accepted surgical procedure. Typically, during such a procedure the diseased lens is removed from the capsular bag by phacoemulsification and a replacement lens is folded, inserted into the capsular bag and allowed to unfold to act as a replacement lens.

Early implantable IOLs did not afford any correction for corneal astigmatism and a patient suffering from such a condition would still have to wear glasses even after the cataract was removed and a new lens inserted in its place.

Alcon Industries has developed its AcrySof® toric IOL which combines the flexibility of an implantable IOL with the astigmatic corrections available in typical glass or plastic eyeglass lenses. In order to use a toric IOL effectively, the lens must be rotated in the capsular bag to align the lens with a pre-calculated optimal axis, typically the steepest curvature of the cornea. To do so, a keratometer is used to measure the patient's cornea and to determine the steep axis of the cornea. When the toric IOL is implanted, a pair of reference marks on the toric IOL are aligned with the steep axis to provide the desired vision correction.

It is important to have an accurate measurement of the corneal curvature and equally important to find a method for identifying the steep axis during surgery so the IOL can be aligned properly.

The present invention relates to instruments which are used to mark the cornea of the patient to identify pre-phacoemulsification reference points to determine the orientation of the steep axis of the cornea so that after phacoemulsification the IOL can be rotated to align it properly with the steep axis.

Prior to phacoemulsification the patient's eye is examined with a keratometer and a toric IOL calculator is then used to determine the angle of the steepest, or "steep" axis along which the astigmatism is most pronounced and with which the lens needs to be aligned. The angle is then noted.

Prior to surgery, the patient is seated in an upright position and a corneal marker is used to mark the 3-, 6- and 9 o'clock positions on the cornea, with the 3- and 9 o'clock positions corresponding to the corners of the eye and the 6 o'clock position corresponding to the bottom of the eye. These will be the reference points for later marking of the steep axis.

The corneal marker includes a series of marking tabs formed on the front surface of a circular ring, placed at 90° intervals. The rear of the ring includes a number of marking tabs intended to come into contact with the cornea. After the marking tabs are coated with dye, one marking tab is aligned with the limbus of the eye and the instrument is then pressed against the cornea to leave marks corresponding to the 3-, 6- and 9 o'clock positions.

A second corneal marker, made specifically for marking the steep axis has a pair of axis marking tabs on the rear and a scale on the front, marked in degrees. Some corneal markers may also includes a rotating ring, commonly mounted within a fixed ring, with the fixed ring used to mark the reference points and a rotating ring used to mark the steep axis. The rotating ring has a pair of axis marking tabs formed on its rear surface.

When the patient is lying down ready for surgery, one of the corneal markers described above is used to mark the steep axis. If the second corneal marker has a fixed set of tabs, the scale on the front of the marker is read to correspond with the steep axis by aligning the axis reading with the reference points already present on the cornea. If a corneal marker with a rotating ring is used, the marker is aligned with the reference points and the ring is rotated until the steep axis setting is reached and the marker is allowed to come into contact with the cornea to press the axis tabs, aligned with the angle marking on the marker, against the cornea. The axis tabs make a pair of marks on the cornea, and it is this second set of reference marks that identifies the axis with which the IOL is aligned when it is inserted so that the stigmatic correction of the IOL is maximized.

The corneal marker will work more accurately to make the reference marks if it is held in a horizontal position when the patient is sitting up. To position the marker, the user hold it to align the handle in a generally horizontal orientation. The marker will work most accurately if it is held in a horizontal position when the patient's eyes are also aligned horizontally, as in when the patient is sitting up. To position the marker, the user holds it in as horizontal an orientation as possible, aligns the marker with the patient's eye and then presses it against the eye so that the dye-coated axis tabs make the desired reference marks on the cornea. It is important for the corneal marker to be held as nearly level as possible during the marking process.

Examples of markers and tilt detectors are found in the prior art.

U.S. Pat. No. 6,217,596 (Farah) teaches and describes a corneal surface and pupillary cardinal axes marker having an inclinometer mounted on the frame.

U.S. Patent Application Publication 2008/0228210 (Davis) describes prior art markers having level gauges or plumb bobs to indicate when the marker handle is being held in the horizontal position.

U.S. Pat. No. 4,739,761 teaches and describes a cornea marker that employs a rotating marker wheel to allow the cornea to be marked at selected locations.

It is an object of the present invention to provide instruments useful for marking the cornea for the insertion and alignment of a multifocal IOL while allowing the surgeon to double check the location of the corneal steep axis prior to insertion of the lens.

It is a further object of the present invention to provide a convenient and accurate way in which to assure that the corneal marker and the patient's eye are properly aligned to make an accurate measurement.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

These and further objects of the present invention will become more apparent upon considering the accompanying drawings in which:

FIG. 1 is a perspective view of a prior art corneal reference marker;

FIG. 2 is a detail of the marking end of the marker shown in FIG. 1;

FIG. 3 is a perspective view of a prior art corneal axis marker;

FIG. 4 is a top detail view of the marking end of the marker in FIG. 3;

FIG. 5 is a bottom detail view of the marker in FIG. 3;

DETAILED DESCRIPTION OF THE DRAWINGS

Figure 6:
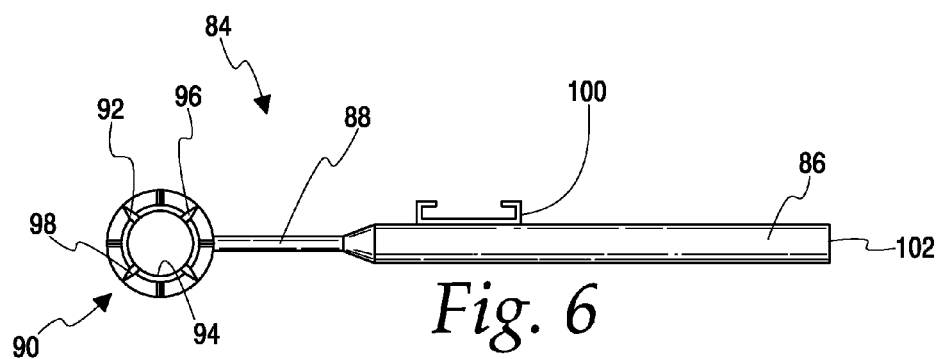
FIG. 6 is a lateral view of a marker embodying certain principles of the present invention.

Referring now to FIG. 1, the numeral 10 identifies a prior art reference marker. Reference marker 10 has a handle 12 tapering at one end to form a throat 14 to which a marker blade 16 is integrally, fixedly and non-rotatably attached. As seen in FIG. 1, blade 16 has an upper surface 18 and a lower surface 20 and is preferably formed as a semicircular flat segment. As best seen in FIG. 2, blade 16 has first and second marking tabs 22, 24 formed diametrically opposite one another and formed integrally with blade 18. Tab 22 has an upper marking edge 26 and a lower marking edge 28 while tab 24 has an upper marking edge 30 and a lower marking edge 32.

A third marking tab 34 is formed integral with upper surface 18 and midway along blade 16 between first and second marking tabs 22, 24. Tab 34 has an upper marking edge 36. A fourth marking tab 38 having a lower marking edge 40 extends from lower surface 20 opposite third marking tab 34.

While the marking tabs 22, 24, 34 and 38 are shown in FIGS. 1 and 2 as elongated "knife edges" other shapes can be used for the marking tabs. For example, raised hemispherical dots can also be used. The shape of the marking tab can determine the shape and size of the mark left on the cornea.

Referring now to FIG. 3, the numeral 42 identifies an axis marker having a handle 44 tapering to a throat portion 46 to which a mounting fork 48 is integrally attached at a preselected and nonadjustable angle.

Attached to fork 48 is a combined gauge and keratometer assembly 50. As best seen in FIGS. 4 and 5, assembly 50 comprises a toroidal gauge ring 52 having an upper surface 54 onto which a scale marked off in degrees from zero to 180 is engraved. Ring 52 is attached to fork 48 such that a 90° marking on the scale is positioned at fork 48. Ring 52 does not rotate with respect to fork 48.

Gauge ring 52 has a central circular aperture 56 formed therethrough. An inner toroidal marker ring 58 is rotatably fitted to gauge ring 52 through aperture 56. Ring 58 has a first right circular segment 60 held rotatably within the gauge ring 52 with first segment 60 extending above upper gauge ring surface 54. A reference mark 62 is engraved on ring 58.

Referring now to FIG. 5, pair of locating tabs 70, 72 are formed on the lower surface of gauge ring 52 preferably to coincide with the 90/90° marks on top surface 54 of ring 52. Also as seen in FIG. 5, a pair of marking tabs 74, 76 are formed on the lowermost surface of third marker ring segment 64. As can be appreciated, marking edges 74, 76 will rotate as marker ring 58 is rotated.

A keratometer ring 78 is attached to inner wall 80 of marker ring 58 by ring shaft 82. When axis marker 42 is placed on a patient's cornea, light from the operating microscope is directed through keratometer ring 78 and will highlight the general shape of any astigmatism in the cornea. This is not intended as a precise identification of the position of the "steep axis" of the cornea, but is intended to provide a backup indicator to confirm to the surgeon that the previously obtained keratometer readings were correct in identifying the steep axis.

In use, marking tabs 74, 76 are coated with a suitable dye and marker ring 58 is rotated to bring reference mark 62 in alignment with the scale scribed on surface 54 to coincide with the angle of the previously-measured steep axis. Non-rotating markers 70, 72 are then coated with a suitable dye. The instrument is then placed on the eye to bring one of the non-rotating tabs 70, 72 at the corner of the eye such that tabs 74, 76 are in alignment with the steep axis. Tabs 74, 76 are then pressed against the cornea to leave a pair of marks that allow the surgeon to align the IOL along the steep axis after insertion.

As shown in FIGS. 4 and 5, ring 78 is formed with a single ring, but multiple concentric rings can also be used to provide differing light patterns and effects as desired.

Referring now to FIG. 6, the numeral 84 identifies generally a corneal marker having a handle 86 from which extends a throat 88. A keratometer assembly 90 is mounted to the distal end of throat 88 and includes a fixed marked scale 92 and an inner rotating ring 94 to which indexing markers 96, 98 are attached.

It is to be understood that keratometer assembly 90 is assembled and functions generally in accordance with the foregoing descriptions of keratometer assemblies having rotating index rings and having marking tabs formed on the rotating and non-rotating portions of the assembly. In the view shown in FIG. 6, the marking tabs are on the reverse side of keratometer assembly 90 and are not visible.

A tilt detector mount 100 is attached to handle 86 intermediate throat 88 and handle end 102.

Figure 7:
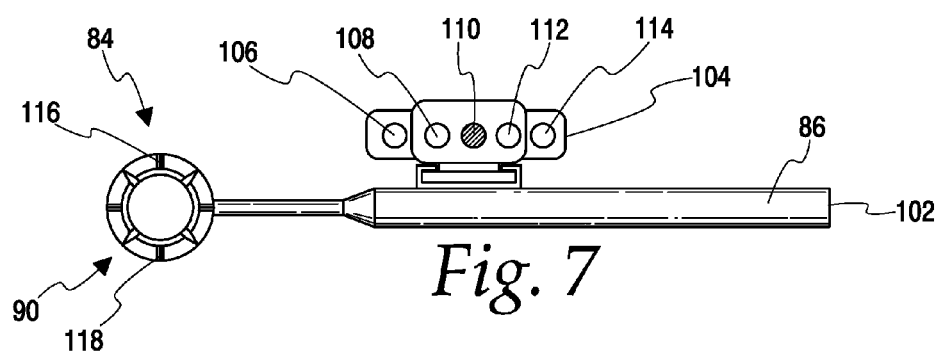
FIG. 7 is a lateral view of the marker of FIG. 6 with a tilt detector secured thereto.

Referring now to FIG. 7, the numeral 104 identifies a tilt detector of the type having a series of light emitting diodes (LED's) 106, 108, 110, 112 and 114. Such a device is marketed by Velbon and is identified as an action level.

As tilt detector 104 is inclined with respect to the horizontal, various of the LED's 106, 108, 110, 112, and 114 will sequentially light up to identify the orientation of tilt detector 104 and thereby handle 86. For example, if handle 86 is inclined to the right with keratometer assembly 90 being higher than handle end 102, LEDs 106, 108 will be illuminated. In similar fashion, if marker 84 is tilted such that keratometer assembly 90 is lower than handle end 102, LEDs 112, 114 will be illuminated. When center LED 110 is illuminated, handle 86 is in a horizontal position which means that reference marks 116, 118 are aligned vertically.

Tilt detector 104 is of the type that can also emit a characteristic sound when it is level and LED 110 is lit.

Use of corneal marker 84 is enhanced when the patient's head is positioned so that the patient's eyes are horizontally level.

Figure 8:
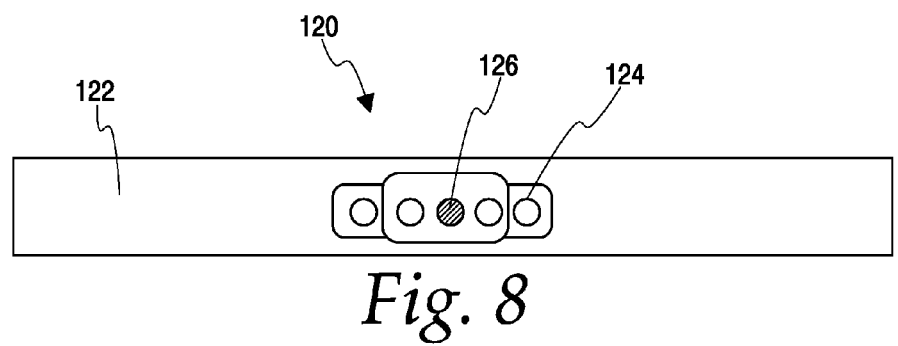
FIG. 8 is a plan view of a headband having a tilt detector.

Referring now to FIG. 8, the numeral 120 identifies a headband assembly comprising a headband 122 to which a tilt detector 124 is attached. In this embodiment, the construction, function and operation of tilt detector 124 is similar to that of device 104. When headband 120 is held in a horizontal position, central LED 126 will be illuminated. In addition, tilt detector 124 can also emit an audible sound signal to indicate that it is in the level position. The remaining LEDs on tilt detector 124 serve as a visual indicator to the user that headband 122 is not level and indicates the direction in which headband 122 must be inclined to be level.

In use, headband 122 is placed around the patient's forehead as the patient is in a seated position. The patient's head is moved to produce a signal that the headband and, thereby, the patient's head are in a position to horizontally level the patient's eyes.

Corneal marker 84 is placed near the eye to be marked and handle 86 is inclined until a similar level signal is produced by tilt detector 104. When both tilt detectors 104, 124 are producing leveling signals, then keratometer assembly 90 is correctly oriented to mark the patient's eye.

Figure 9:
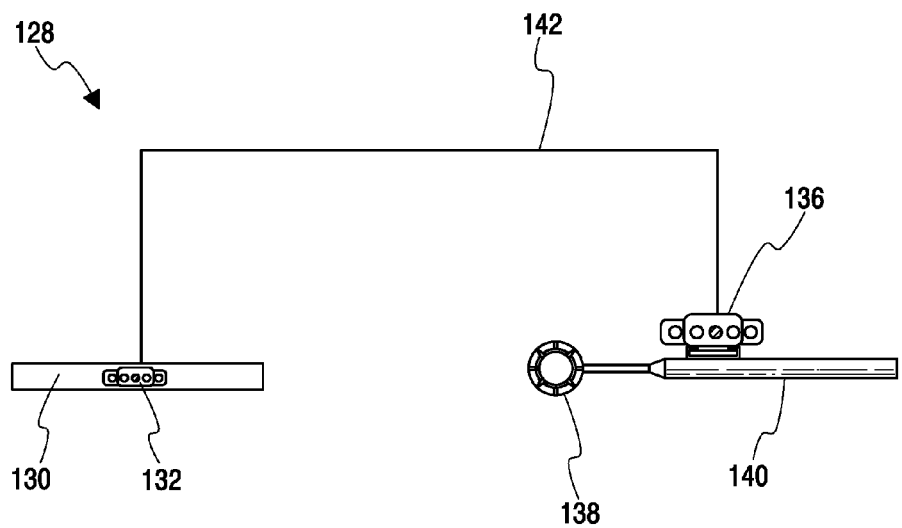
FIG. 9 is a view of the aforesaid marker and headband being used in tandem.

Referring to FIG. 9, an alternate embodiment of the present invention is illustrated. Leveling assembly 128 has a headband 130 to which a tilt detector 132 is affixed. A corneal marker 134 is also provided having a tilt detector 136 thereon and operating such that keratometer assembly 138 may be leveled by manipulating handle 140.

A communication pathway 142 extends between devices 132 and 136. Pathway 142 may consist of an electrically conductive wire and may also indicate a pathway created wirelessly by broadcast and receiving circuits provided in tilt detectors 132, 136.

Tilt detectors 132, 136 are adapted to communicate to each other and to indicate the degree to which each is inclined with respect to a selected reference. In the most common case, the selected reference will be the horizontal direction. Using the arrangement of FIG. 9, it is not necessary to have headband 130 aligned to a horizontal position and to have marker 134 aligned to a horizontal position. Instead, tilt detectors 132, 136 are adapted to emit either a visual or audible signal when both are oriented alike. Thus, if headband 130 is aligned to an inclination of 5° from true horizontal, a confirming signal will be broadcast when corneal marker 134 is also inclined to 5° from true horizontal. In this manner, headband 130 and corneal marker 134 can be properly oriented without requiring separate leveling observations on independently operating tilt detectors and without requiring both to be horizontally level.

Figure 10:
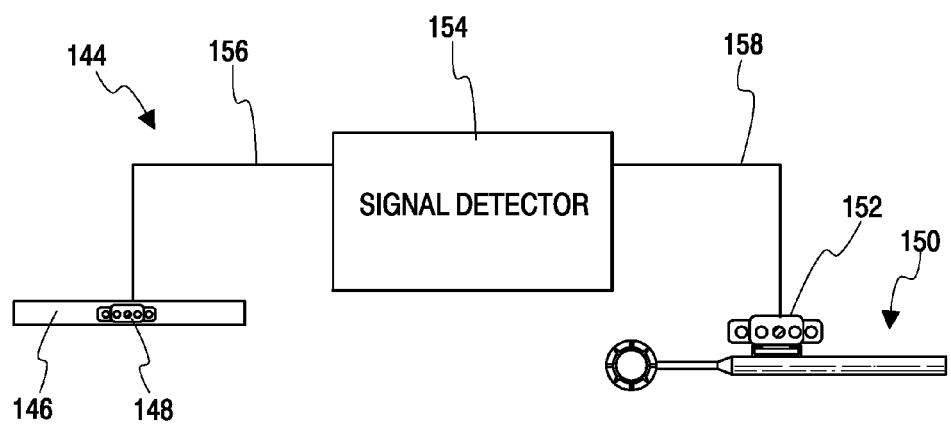
FIG. 10 is another embodiment of the arrangement of FIG. 9.

Referring now to FIG. 10, an alternate arrangement of the leveling assembly of FIG. 9 is shown. Leveling assembly 144 is shown having headband 146 to which a tilt detector 148 is attached, and a corneal marker 115 to which a tilt detector 152 is attached. A signal detector 154 is provided and is connected such that a first communication passageway 156 extends from tilt detector 148 to signal detector 154 and a second communication pathway 158 extends from tilt detector 152 to signal detector 154.

Using such an arrangement, signal detector 154 can audibly, visually, or a combination thereof, indicate when tilt detectors 148, 152 are held in identical orientations with respect to a selected reference. As described above, communication passageway 156, 158 can be wired or wireless.

As seen in FIGS. 6 and 7, the tilt detector associated with each of both described corneal markers may be removed to allow the corneal marker to be sterilized. The tilt detector can be inserted from either side of the mount so that the corneal marker can be aligned to be used with both left and right eyes. Alternatively, a set of LEDs can be positioned on both sides of the tilt detector so it can be read from front or rear.

It is also contemplated that a tilt detector constructed to withstand the sterilization process can be mounted in the handle itself.

If it is desired to keep patient distractions to a minimum when using the audible signal to verify alignment the signal can be set to broadcast to a set of headphones or an earpiece. The readings of both the corneal marker and the headband can be stored in a computer to make a full record of the patient's procedure for later review.

In use, the patient is first fitted with a headband constructed in accordance with the foregoing. Where there is a preset inclination, the patient is assisted to reach a head position where the preset is met as indicated by the signal generated by the tilt detector mounted on the headband. Next, a corneal marker, constructed as set forth herein, is selected, having a tilt detector with a preset inclination matching that of the headband. The corneal marker is adjusted to produce a signal confirming that the headband and the corneal marker are both aligned to the same preset inclination and the marking of the cornea is then carried out.

Where there is no preset inclination, the headband tilt detector and the corneal marker tilt detector are set to emit a signal when both are aligned to the same inclination. Once this signal is produced corneal marking can proceed. In this manner, even if the patient's head moves, an accurate reading will still be obtainable.

What is claimed is:

1. A system for marking a cornea of an eye of a patient, said system comprising:
   a corneal marker having
      a handle with proximal and distal ends,
      a keratometer mounted to said handle at said distal end, said keratometer including a plurality of marking tabs configured to place a plurality of selected marks on said cornea when said plurality of marking tabs are brought into contact with said cornea, and
      a first tilt detector mounted to said handle intermediate said proximal end and said distal end, said first tilt detector configured to detect a tilt of said handle, said first tilt detector configured to emit at least one of an audio signal and a visual signal when said first tilt detector is aligned to a preset tilt value; and
   a second tilt detector configured for being affixed to said head of said patient, said second tilt detector configured for detecting a tilt of said patient's head, said second tilt detector configured to emit at least one of an audio signal and a visual signal when said second tilt detector is aligned to said preset tilt value of said first tilt detector, wherein said second tilt detector includes a headband assembly for being secured to said patient's head.

2. The system as recited in claim 1 wherein said preset tilt value is horizontal.

3. The system as recited in claim 1 wherein said first tilt detector is removably attached to said handle.

4. A system for marking a cornea of an eye of a patient, said system comprising:
   a corneal marker having
      a handle with proximal and distal ends, a keratometer mounted to said handle at said distal end, said keratometer including a plurality of marking tabs configured to place a plurality of selected marks on said cornea when said plurality of marking tabs are brought into contact with said cornea, and a first tilt detector mounted to said handle intermediate said proximal end and said distal end, said first tilt detector configured to detect a tilt of said handle; and a second tilt detector configured for being affixed to said head of said patient for detecting a tilt of said patient's head;

said first and second tilt detectors configured to emit at least one of an audio signal and a visual signal when said first and second tilt detectors are aligned to a preset tilt value, wherein said second tilt detector includes a headband assembly for being secured to said patient's head.

5. The system as recited in claim 4 wherein said first tilt detector is removably attached to said handle.

6. The system as recited in claim 4 further comprising a communication pathway between said first and second tilt detectors.

7. The system as recited in claim 6 wherein said communication pathway comprises an electrically-conductive wired connection.

8. The system as recited in claim 6 wherein said communication pathway comprises a wireless connection between said first and second tilt detectors.

9. The system as recited in claim 6 wherein said communication pathway is configured to allow two-way signal transmission between said first and second tilt detectors.

10. The system as recited in claim 9 further comprising a signal detector within said communication pathway for comparing a first signal from said first tilt detector with a second signal from said second tilt detector, said signal detector being configured to produce a third signal when said first and second signals indicate substantially the same value for a respective tilt of said corneal marker and said patient's head.

11. A method for marking a cornea of an eye of a patient, said method comprising the steps of:
 obtaining a system having;
  a corneal marker having
   a handle with proximal and distal ends,
   a keratometer mounted to said handle at said distal end, said keratometer including a plurality of marking tabs configured to place a plurality of selected marks on said cornea when said plurality of marking tabs are brought into contact with said cornea, and
   a first tilt detector mounted to said handle intermediate said proximal end and said distal end, said first tilt detector configured to detect a tilt of said handle, said first tilt detector configured to emit at least one of an audio signal and a visual signal when said first tilt detector is aligned to a present tilt value; and a second tilt detector configured for being affixed to said head of said patient,
   said second tilt detector configured for detecting a tilt of said patient's head,
   said second tilt detector configured to emit at least one of an audio signal and a visual signal when said second tilt detector is aligned to said preset tilt value of said first tilt detector, wherein said second tilt detector includes a headband assembly for being secured to said patient's head;
 aligning said keratometer with an eye of a patient; and
 applying a plurality of marks to said eye with said plurality of marking tabs when said at least one of an audio signal and a visual signal is emitted by said first tilt detector.

12. The method of claim 11 further comprising the step of:
 affixing said second tilt detector to a head of said patient.

13. A method for marking a cornea of an eye of a patient, said method comprising the steps of:
 obtaining a system having;
  a corneal marker having
   a handle with proximal and distal ends,
   a keratometer mounted to said handle at said distal end, said keratometer including a plurality of marking tabs configured to place a plurality of selected marks on said cornea when said plurality of marking tabs are brought into contact with said cornea, and
   a first tilt detector mounted to said handle intermediate said proximal end and said distal end, said first tilt detector configured to detect a tilt of said handle,
   a second tilt detector configured for being affixed to said head of said patient for detecting a tilt of said patient's head;
   said first and second tilt detectors configured to emit at least one of an audio signal and a visual signal when said first and second tilt detectors are aligned to a preset tilt value, wherein said second tilt detector includes a headband assembly for being secured to said patient's heads, a communication pathway between said first and second tilt detectors, said communication pathway is configured to allow two-way signal transmission between said first and second tilt detectors; and
   a signal detector within said communication pathway for comparing a first signal from said first tilt detector with a second signal from said second tilt detector, said signal detector being configured to produce a third signal when said first and second signals indicate substantially the same value for a respective tilt of said corneal marker and said patient's head;
 affixing said second tilt detector to a head of a patient;
 aligning said keratometer with an eye of said patient;
 applying a plurality of marks to said eye when said third signal is emitted.

* * * * *